(12) United States Patent
Prokoshkin et al.

(10) Patent No.: US 7,955,449 B2
(45) Date of Patent: Jun. 7, 2011

(54) PROCESS FOR INDUCING A TWO-WAY SHAPE MEMORY EFFECT IN A DEVICE FORMED OF A SHAPE MEMORY ALLOY AND A DEVICE MADE BY THE PROCESS

(75) Inventors: Sergey Dmitrievich Prokoshkin, Moscow (RU); Irina Yurievna Khmelevskaya, Moscow (RU); Elena Prokopievna Ryklina, Moscow (RU)

(73) Assignee: Intek Technology, L.L.C., Wilmington, DE (US)

( * ) Notice: Subject to any disclaimer, the term of this patent is extended or adjusted under 35 U.S.C. 154(b) by 540 days.

(21) Appl. No.: 12/175,032

(22) Filed: Jul. 17, 2008

(65) Prior Publication Data
US 2010/0016952 A1  Jan. 21, 2010

(51) Int. Cl.
*C22F 1/00* (2006.01)
*A61F 2/06* (2006.01)
(52) U.S. Cl. ...................... 148/563; 623/1.18
(58) Field of Classification Search .................. 148/563; 623/1.18
See application file for complete search history.

(56) References Cited

U.S. PATENT DOCUMENTS

| 4,984,581 A | 1/1991 | Stice |
| 5,624,508 A | 4/1997 | Flomenblit et al. |
| 5,836,066 A | 11/1998 | Ingram |
| 5,882,444 A | 3/1999 | Flomenblit et al. |

OTHER PUBLICATIONS

A. Mehta et al., "On the Electronic and Mechanical Instabilities in Ni50.9Ti49.1", Material Science and Engineering A 378 (2004) pp. 130-137.

*Primary Examiner* — Roy King
*Assistant Examiner* — Jessee R. Roe
(74) *Attorney, Agent, or Firm* — Cozen O'Connor (57) ABSTRACT

A process for inducing a two-way shape memory effect in a device forward of a shape memory alloy and a device made by the process are disclosed. The two-way memory effect occurs in the device in a temperature range of between about 5° C. to 25° C. wherein the training process is based on B2↔R phrase transformations. An R-phase formation or reorientation takes place in the device under stress whereupon the R-phase transforms into stress induced martensite. The device is subjected to thermocycling.

35 Claims, 6 Drawing Sheets

PROCESS FOR INDUCING A TWO-WAY SHAPE MEMORY EFFECT IN A DEVICE FORMED OF A SHAPE MEMORY ALLOY AND A DEVICE MADE BY THE PROCESS

FIELD OF THE INVENTION

This invention relates generally to the manufacture of devices formed of shape memory alloys and, more particularly, to processes for inducing a two-way shape memory effect in devices formed of a SMA.

BACKGROUND OF THE INVENTION

The special properties of a shape memory alloy (SMA), such an alloy of nickel and titanium, known as nitinol, have enabled the creation of a new generation of medical devices. Unlike traditional metals or alloys such as stainless steel, titanium and tantalum, such alloys exhibit shape memory properties through a solid to solid phase change which occurs with a change of temperature over a certain range. A plastically deformed device formed of a SMA when heated over a certain temperature range will "remember" its original shape and return to it.

The shape recovery of a plastically deformed device formed of a SMA upon heating is called "one-way shape memory effect." The more important parameters of a one-way shape memory effect include recovery strain ($\epsilon_r$), shape recovery rate, recovery stress ($\sigma_r$) and the temperatures at which direct martensitic and austenitic, i.e. reverse martensitic, transformations occur, designated $M_s$, $M_f$, $A_s$ and $A_f$.

As used herein, in the case of Ni—Ti alloy, enriched with nickel and aged, there is a two-stage transformation upon heating or cooling. $M_s$ designates the martensite start temperature which is the temperature at which the transformation from the intermediate R-phase to martensite begins on cooling; $M_f$ designates the martensite finish temperature which is the temperature at which the transformation from R-phase to martensite is completed upon cooling; $A_s$ designates the austenite start temperature which is the temperature at which the transformation from the R-phase to austenite begins on heating; and $A_f$ designates the austenite finish temperature which is the temperature at which the R-phase to austenite transformation is completed on heating.

A two-way shape memory effect (TWSME) can be induced in a device formed of a SMA by a single or repeated deformations of the device in conjunction with thermocycling through a temperature range over which martensitic and austenitic transformations occur ("a so-called training"). Devices formed of a SMA having an induced TWSME "remember" both their low temperature shape and high temperature shape, so that appropriate cooling of a device formed of a SMA in which a two-way memory has been induced will cause the device to return towards its deformed shape.

A TWSME of a SMA is characterized by its own TWSME parameters including two-way recovery strain ($\epsilon_{TW}$), shape recovery rate, recovery stresses ($\sigma_r$) and temperature ranges over which a shape recovery occurs. The value of these parameters can be adjusted by subjecting a device formed of a SMA to certain thermomechanical and heating treatments. Moreover, the stability of the two-way recovery strain and the temperature range over which a TWSME occurs is of great practical importance.

Several circumstances must be taken into account when training a device formed of a SMA to have TWSME, especially in medical applications such as endovascular stents:

1. The two-way recovery strain ($\epsilon_{TW}$) must be at a sufficiently high level to provide the required functionality of the device.

2. The temperature ranges (cooling and heating) over which the two-way shape change is realized must be appropriate for the application (for example, in endovascular stents situated in a blood vessel, heating to a temperature not higher than the temperature of blood coagulation, i.e., about 42° C., and cooling to a temperature not below about 10° C.).

3. The requirements of items 1. and 2. become even more important when reiterative shape changing upon heating and cooling is necessary. Under such circumstances, the stability of the two-way recovery strain ($\epsilon_{TW}$) and the temperature ranges over which the two-way shape changes occur become very important.

4. The TWSME parameters of the SMA should be substantially constant during thermocycling through the temperature ranges over which the two-way shape changes occur, as well as during subsequent storage of devices made from the SMA.

5. Even after accidental heating of the SMA device over the final temperature of shape recovery $A_f$, the two-way recovery strain ($\epsilon_{TW}$) and the temperature ranges over which the two-way shape changes occur must remain stable.

Any reduction in the two-way recovery strain must be minimal, and the two-way shape changes must still occur within the required temperature ranges.

At the same time, the properties of Ni—Ti alloys must be taken into account:

1. The shape change and shape recovery of medical devices, such as stents, formed of a SMA having an induced TWSME are realized by austenite (B2)→intermediate R-phase (R)→martensite (B19') and B2→R→B19' phase changes, respectively. A TWSME is realized by setting up permanently acting oriented microstress fields by strain hardening (under external stress) or by transformation induced hardening under B2↔R↔B19' phase transformations or by oriented coherent precipitates.

2. Continued phase transformation induced hardening and strain hardening have their own influences upon temperatures of B2↔R and R↔B19' transformations. According to different sources this influence is ambiguous. These changes are at their maximum in the initial phase transformation cycles (or in the initial cycles of active deformation), and gradually degrade with subsequent cycles. As a result, the difference between $T_R$ and $M_S$ in the initial cycle can reach 60°-80° C. after ageing. The foregoing factors should be taken into account in connection with TWSME training of a device formed of a SMA by providing that the $A_s$ and $A_f$ temperatures of the SMA device should be significantly lower than their respective values for the finished TWSME trained device.

3. The influence of external action parameters of TWSME training, e.g. strain and loading modes, loading temperature regime or phase state, load value, loading time and number of training cycles, on the magnitude of the $\epsilon_{TW}$ should be taken into account. It is well-known that external action parameters of TWSME strongly affect kinetics and final TWSME parameters.

Various techniques for inducing a TWSME in a SMA have been suggested. For example, see U.S. Pat. Nos. 5,624,508, 5,836,066, 5,882,444 and 6,596,192. The '508 and '444 patents disclose subjecting a SMA to various combinations of heat and thermomechanical treatments (including ageing, polygonizing annealing and recrystallizing annealing) to induce a TWSME. These techniques have not proven to be satisfactory.

For example, known methods of TWSME training do not achieve sufficiently high values of $\epsilon_{TW}$ in the preferred temperature range of 10° C.-37° C. in which shape changes of medical devices such as stents formed of SMA having TWSME should occur.

Known TWSME training techniques are based on martensitic transformations and experience has shown that thermocycling through a full temperature range of martensitic transformation(s) results in decreases of transformation critical temperatures which in turn downwardly shift the temperature range over which the shape-changing TWSME transformations occur.

Moreover, known TWSME training methods do not provide thermal stability of the TWSME parameters induced through R-phase. The two-way memory effect degrades when the SMA is heated above $A_f$ and is not fully restored with repeated thermal cycling.

SUMMARY OF THE INVENTION

Accordingly, it is an object of the present invention to provide a new and improved process for treating a SMA to induce a TWSME.

It is another object of the present invention to provide new and improved TWSME training processes which are particularly suitable for medical devices, such as endovascular stents.

Still another object of the present invention is to provide new and improved processes for inducing TWSME in medical devices formed of SMA which provide a sufficiently high value of $\epsilon_{TW}$ and an appropriate temperature range over which two-way shape changes are realized.

A further object of the present invention is to provide new and improved TWSME training procedures for medical devices such as stents in which the two-way shape changes occur in a temperature range of between about 37° C. to a temperature in the range of between about 5°-25° C. based on R-phase transformation(s).

A still further object of the present invention is to provide new and improved methods for inducing a TWSME in a device made of a SMA in which the device manifests its initial shape in the austenitic phase and manifests its final shape in the R-phase.

Yet another object of the present invention is to provide new and improved TWSME training procedures which provide thermal and mechanical stability of the TWSME.

Yet a further object of the present invention is to provide a new and improved medical device formed of a SMA having TWSME.

Briefly, in accordance with the present invention, these and other objects are attained by providing methods for training a SMA in which a two-way memory effect occurs in a temperature range of between about 37° C. and a temperature in the range of between about 5° C.-25° C. wherein the training methods are based on B2 ↔ R phase transformations, i.e., the training occurs above the $M_s$ temperature.

The invention is based on performing a reorienting deformation of a device formed of a Ni—Ti alloy either in the R-phase or B2-phase, or in a mixed B2-R phase formation, i.e., the temperature of the TWSME training is associated with $T_R$, $A_s$ or $A_f$, but not with $M_s$. First, the R-phase formation or the R-phase reorientation takes place under stress whereupon the R-phase transforms into stress induced martensite. The device is subjected to thermomechanical cycling for increasing and stabilizing $\epsilon_{TW}$ as well as the temperature range of TWSME. The TWSME is realized in the B2 ↔ R temperature range with a maximum recovery strain $\epsilon_{TW}$ of about 1.2% (1.15% theoretically and 1.37% experimentally). Further increases of $\epsilon_{TW}$ are possible when cooling under 0° C. due to the R ↔ B19' transformation.

A device formed of a SMA having a TWSME according to the invention exhibits an initial shape in the austenitic phase and a final shape in the R-phase.

Three embodiments of a training method in accordance with the invention are disclosed. In each case, the SMA of which the device is formed is nitinol having an $A_f$ temperature of between about 25°-35° C. and a $T_R$ temperature of between about 5°-25° C. Each embodiment of the process results in a device that exhibits spontaneous transformation from an initial shape which the device manifests in an austenitic phase memory state to a final shape which the device manifests in the R-phase memory state.

In a first embodiment, the steps include loading the device at a temperature within a range designated $T_1$, wherein $T_R<T_1<A_f+30°$ C., cooling the device while in a loaded condition to a temperature within a range designated $T_2$ wherein $T_R-30°$ C.$<T_2<T_R$, maintaining the device in a loaded state at a temperature in the range $T_2$ for a period of time, unloading the device, and thermocycling the unloaded device, wherein each thermocycle includes heating the unloaded device to a temperature within a range designated $T_3$ wherein, $A_f<T_3<A_f+30°$ C., and cooling the unloaded device to a temperature in the range $T_2$. As used throughout this application including the claims, the term< means "less than about".

In a second embodiment, the steps include loading the device at a temperature in the range $T_1$, wherein $T_R<T_1<A_f+30°$ C., cooling the device in its loaded condition to a temperature in the range $T_2$, wherein $T_R-30°$ C.$<T_2<T_R$, maintaining the device in a loaded state at a temperature in the range $T_2$ for a period of time, thermocycling the device under load wherein each thermocycle includes heating the device in its loaded condition to a temperature in the range $T_3$, wherein $A_f<T_3<A_f+30°$ C., and cooling the device in its loaded condition to a temperature in the range $T_2$, unloading the device, and thermocycling the device in an unloaded condition wherein each thermocycle includes heating the unloaded device to a temperature in the range $T_3$ and then cooling the unloaded device to a temperature in the range $T_2$.

In a third embodiment, the steps include loading the device at a temperature in the range $T_2$ wherein $T_R-30°$ C.$<T_2<T_R$, maintaining the device in a loaded state at a temperature in the range $T_2$ for a period of time, unloading the device, and then thermocycling the unloaded device, wherein each thermocycle includes heating the device to a temperature $T_3$ wherein $A_f<T_3<A_f+30°$ C. and cooling the device to a temperature in the range $T_2$.

In order to obtain a sample of SMA having an $A_f$ temperature of between about 25°-35° C. and a two-way recovery strain of $\epsilon_{TW}$ greater than about 0.2%, when testing, for use in the above-identified method, a sample of the SMA is preferably subjected to a prior thermomechanical treatment as follows:

(a) the raw nickel-titanium based nitinol alloy (in the form of a rod, a wire, a tube or the like) is heated to a temperature in the range of between about 600° C.-800° C. for about 5-30 minutes to obtain a recrystallized structure;

(b) the nitinol is subjected to a low-temperature thermomechanical treatment (LTMT) comprising plastic deformation (e.g. drawing, rolling, expanding or the like) in the austenitic or martensitic phase at a temperature in the range of between and about 0° C.-240° C. with accumulated strain C between about 15% and 40% in order to obtain a well-developed dislocation substructure;

(c) the alloy is shaped into a first shape using conventional tools to form a device; and (d) the device is subjected in a fixed condition to an ageing heat treatment at about 300° C.-440° C. for about 0.25-10 hours to memorize the initial shape followed by quenching the device in water at a temperature in the range of between about 0° C.-25° C. to obtain a well-developed polygonized dislocation substructure and a one-way shape memory effect.

It is to be noted that the results obtained in (d) above depend significantly on the history of the melting process and any prior thermomechanical treatments to which the device may have been subjected.

At that time, the device is tested to ascertain whether the $A_f$ temperature is in the range of between about 25° C.-35° C. and the $T_R$ temperature is in the range of between about 5° C.-25° C., and to ascertain whether the two-way recovery strain $\epsilon_{TW}$ is about 0.2%. A test comprises bending the device around a mandrel into a second shape at a temperature T, wherein $T_R-30<T<T_R$. The ratio of the thickness or diameter ("b") of the device to the diameter of the mandrel (D) is b/D, wherein 0.02<b/D<0.2. The device is then unloaded from the mandrel at about the same temperature. The device is then heated to about $A_f$ at which the transformation to austenite is completed. The device is then cooled again to a temperature T, wherein $T_R-30<T<T_R$. In this manner the device is conditioned to manifest a spontaneous two-way change in shape between a first shape in the austenitic phase and a second shape in the R-phase.

If the values of the $A_f$ and $T_R$ temperatures and the two-way recovery strain fall within the above-mentioned ranges, the process of inducing the TWSME can begin. However, if the $A_f$ temperature is greater than 35° C. and the $T_R$ temperature does not meet the specified ranges, and the value of the two-way recovery strain is less than about 0.2%, additional heat treatment of the device as described below is preferred.

(a) the device is subjected to a heat treatment at a temperature in the range of between about 560° C.-580° C. for about 10-25 minutes and then quenched in water at a temperature in the range of between about 0° C.-25° C. to obtain the mixed polygonized and recrystallized structure;

(b) if necessary, the device is etched (if the heat treatment was performed in a furnace without an inert atmosphere or vacuum), such as in a solution comprising 1 part HF, 3 parts $HNO_3$ and 6 parts $H_2O_2$ to remove any oxide film which may have formed on the surface of the device;

(c) in order to memorize the initial shape, the device is subjected in a fixed condition to an ageing heat treatment at about 300° C.-440° C. for about 0.25 to 10 hours followed by quenching at a temperature of 0° C.-25° C.;

(d) the device is tested to ascertain if the temperature $A_f$ is in the range of between about 25° C.-35° C. and the temperature $T_R$ is in the range of between about 5° C.-25° C. and (i) if the temperature $A_f$ is lower than 25° C., the device is subjected to an additional intermediate ageing heat treatment according to step (c) above; and if the $A_f$ temperature is greater than 35° C., the device is subjected to a recrystallizing heat treatment according to step (a) followed by an ageing heat treatment according to step (c) and, (ii) if necessary the device is etched according to step (b).

In following each of the three embodiments of the invention described above (and below), there is still a problem with stabilizing the TWSME in that the two-way recovery strain $\epsilon_{TW}$ induced in the device utilizing a process according to the invention degrades when the device is heated above the temperature $A_f$ and does not return to its value when repeated on cooling. In order to provide thermal and long-term TWSME stabilization in a nitinol device that exhibits TWSME based on the R-phase transformation in a temperature range of between about 5° C.-40° C.; with a two-way recovery strain of about 1-3%, the device is subjected to mechanical deformation and then fixed on a mandrel (or simply cooled) at a temperature T, wherein $T_R-30$° C.$<T<T_R$ for a period of between about 1-30 days.

BRIEF DESCRIPTION OF THE DRAWINGS

A more complete appreciation of the present invention and many of the attendant advantages thereof will be readily understood by reference to the following detailed description when considered in connection with the accompanying drawings in which.

DETAILED DESCRIPTION OF THE PREFERRED EMBODIMENTS

In connection with all of the embodiments of the present invention, the temperature range over which surgical devices such as stents undergo reversible changes between initial and final shapes is critical. In particular, a retrievable stent must change from its deformed shape to its original shape at or below the body temperature of a patient, i.e. 37° C., when it is delivered, and must change its shape to one closer to its deformed shape upon cooling, such as to facilitate retrieval or repositioning of the stent. The cooling temperature in the vessel of the patient should not be lower than about 10° C. and is preferably about 25° C. For these reasons, the maximum TWSME should manifest itself over a temperature range of between about 10° C.-37° C.

Referring now to the drawings, detailed descriptions of the preferred embodiments, to which the invention is not limited, will now be described. The invention will be described with particular reference to the application of the method to the preparation of retrievable stents having crowns whose segments move inwardly upon cooling for facilitating retrieval of the stent (see e.g., applicant's assignee's U.S. patent application Ser. No. 10/333,599 filed Jan. 21, 2003 incorporated herein in its entirety) or to stents having bodies which reduce in diameter upon cooling for facilitating retrieval (see e.g., applicant's assignee's U.S. Pat. No. 6,837,901 incorporated herein in its entirety).

In order to prepare the nitinol alloy for training, the alloy, which is typically provided in the shape of rods, wire or tubes, is initially heated or annealed at 600° C.-800° C. for 5-30 minutes in order to recrystallize the grain structure and then water-cooled. The recrystallized alloy is then subjected to a low temperature thermomechanical treatment (LTMT) in which the alloy is plastically deformed into a predetermined shape having a well-developed dislocation substructure. The deformation is carried out in the austenite phase at temperatures below the austenite recrystallization temperature (or in the martensite phase or in a mixture of austenite and martensite). The deformation temperatures may be in the range of between about 0° C.-240° C. In the case where it is intended to manufacture a wire, the mechanical deformation is typically a facilitating wire-drawing procedure. In the case where the intended form of manufacture is a ribbon or band device, the mechanical deformation typically involves rolling. In the case where the intended form of manufacture is a laser-cut stent, the mechanical deformation typically involves expansion of a laser-cut tube. The mechanical deformation is generally performed in several passes with a strain per pass of about 5-40%. The alloy may be subjected to intermediate heat treatment at about 400° C. to 700° C. for about 0.25-2 hours. In order to obtain a well-developed dislocation substructure and a one-way shape memory effect, the accumulated (without intermediate heat treatment) strain in the last passes should be less than 40% and greater than 15%.

It is noted that cold rolling during the LTMT cycle is advantageous in that the structure of the alloy is known after a cold deformation. On the other hand, it is difficult to maintain a constant temperature in a thin wire during a warm rolling operation.

The as-received piece is then subjected to a shape operation using a mandrel to obtain a required shape (the "first shape"). The shaped alloy, fixed in the first shape, is subjected to an ageing heat treatment at about 300° C.-440° C. for about 0.25-10 hours followed by quenching in water to obtain a well-developed polygonized substructure and a one-way memory effect, along with optimum morphology and size of the precipitated phase $Ti_3Ni_4$, and a desired temperature range of shape recovery. It is preferable to perform all of the heat treatment steps in a vacuum or inert atmosphere furnace in order to avoid formation of an oxide film.

Figure 1:
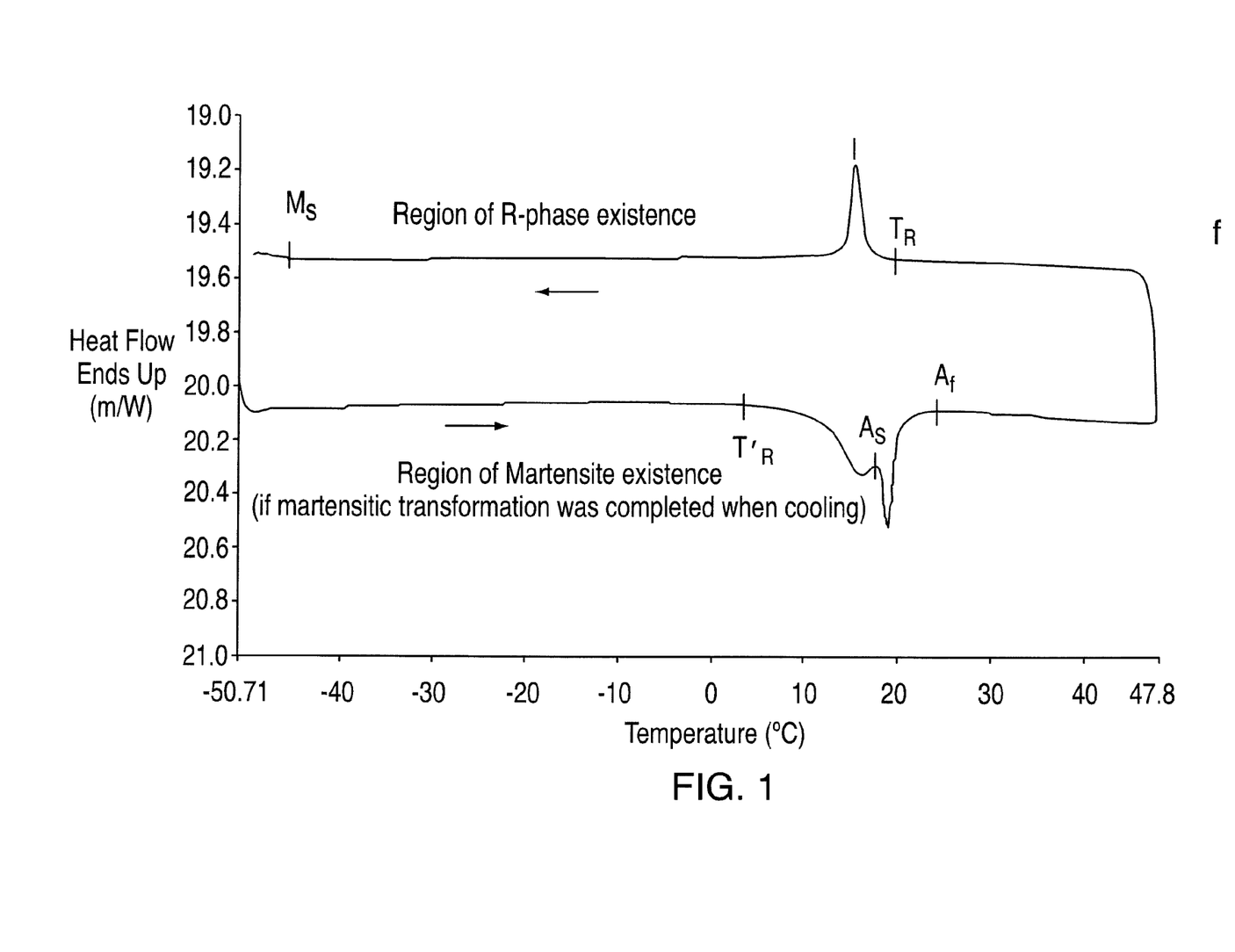
FIG. 1 is a graphical depiction of differential scanning calorimetry (DSC) showing the heating and cooling (from +50° C. to −50° C. at 10° C./min) of a thin wire of Ti (50.7%) Ni alloy after a LTMT and following ageing.

In accordance with the invention, the temperature of TWSME training must be associated with the $T_R$, $A_s$, and $A_f$ temperatures of the SMA alloy. Therefore, the next step is testing the shaped piece ("the device") in order to obtain an $A_f$ temperature in the range of between about 25° C.-35° C. and a $T_R$ temperature in the range of between about 5° C.-25° C. The $A_f$ temperature of the sample must be lower than that of the finished article. The temperature range of training can be attained by known means of differential scanning colorimetry (DSC) (FIG. 1). To simplify the procedure, the $A_s$-$A_f$ range can be determined by visual thermomechanical testing.

The device is then tested to obtain a two-way shape memory effect with a recovery strain of about 0.2%. This is accomplished by bending the device around a mandrel (0.02<b/D<0.2) to a second shape at a temperature T wherein $T_R$-30° C.<T<$T_R$ and preferably in the range of between about 0° C.-10° C., unloading the device at about the same temperature, then heating the device to about $A_f$. At a temperature lower than $T_R$, an R-phase reorientation takes place under stress. Heating to $A_f$ results in the completion of the reverse R-phase reorientation and formation of the austenite phase. The two-way recovery strain is evaluated during the cooling-heating cycle.

If the $A_f$ temperature is between 25° C. and 35° C., the $T_R$ temperature is between 5° C. and 25° C., and the two-way recovery strain $\epsilon_{TW}$ is greater than about 0.2%, it is expedient to begin the TWSME training.

If the $A_f$ temperature is lower than 25° C., then the device is subjected to further heat treatment at a temperature in the range of between about 300° C.-440° C. for about 0.25-10 hours followed by quenching in water at a temperature in the range of between about 0° C.-25° C.

If the $A_f$ temperature is greater than 35° C., then the device is preferably subjected to a heat treatment at a temperature of between about 560° C.-580° C. for about 10 to 25 minutes and then quenched to a temperature of between about 0° C.-25° C. to obtain a mixed polygonized and recrystallized structure and to simultaneously dissolve precipitates. If the heat treatment has been performed in a furnace other than an inert atmosphere or a vacuum, the device is subjected to etching in a solution comprising 1 part HF, 3 parts $HNO_3$ and 6 parts $H_2O_2$ in order to remove any oxide film from the surface of the device.

The $A_f$ temperature drops significantly after the heat treatment and in order to elevate it into the required range, the device is subjected in a fixed condition to an ageing heat treatment at about 300° C.-440° C. for about 0.25-10 hours followed by a quenching to about 0° C.-25° C.

The device is then tested again to determine if the temperature $A_f$ is in the range of between about 25° C.-35° C. and the temperature $T_R$ is in the range of between about 5° C.-25° C. If the $A_f$ and $T_R$ temperatures and the two-way recovery strain $\epsilon_{TW}$ are within the desired ranges, then it is expedient to begin the process of inducing the TWSME in the device.

The characteristic temperatures of phase transformations $T_R$, $A_S$, $A_F$ are shown in the Figures as follows:

FIG. 1 is a graphical description showing the results of differential scanning calorimetry of a thin wire formed of 50.7% nickel and 49.3% titanium after the LTMT and ageing heat treatment.

Figure 2A:
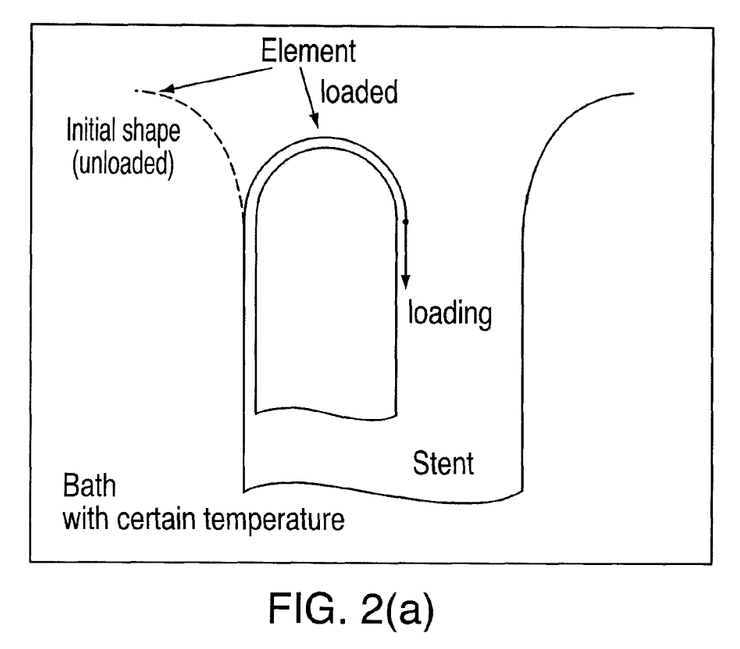
FIGS. 2(a) and 2(b) are schematic illustrations showing two arrangements for inducing TWSME in a segment of a crown of a stent by loading the segment around a mandrel.
Figure 2B:
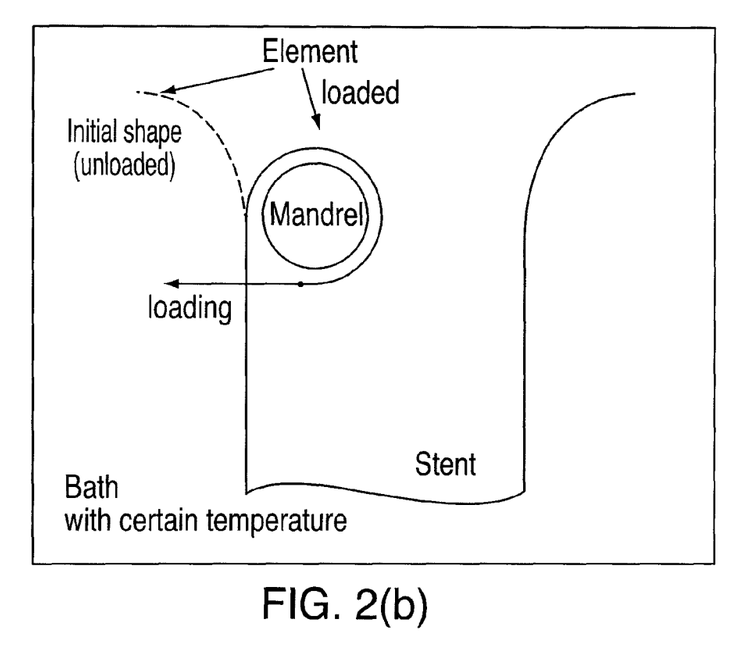

FIGS. 2(a) and 2(b) show arrangements for inducing a TWSME in a segment of a stent crown comprising, e.g., 6 segments. Such a crown is disclosed in applicants' assignee's U.S. patent application Ser. No. 10/333,599 filed Jan. 21, 2003, the disclosure of which is incorporated by reference in its entirety. In conformity with the illustrated embodiments, the inducement of a TWSME is preferably performed using a bending scheme providing a total strain $\epsilon_t$=3-17%, with an applied tension $\sigma$=0-50 $MP_a$. The device should be deformed near or somewhat above the limit of the one-way recovery strain. The exposure time of the device in its constrained condition can reach 1 minute. Of course, other loading arrangements than those described and illustrated can be utilized for training devices other than stents.

Figure 3:
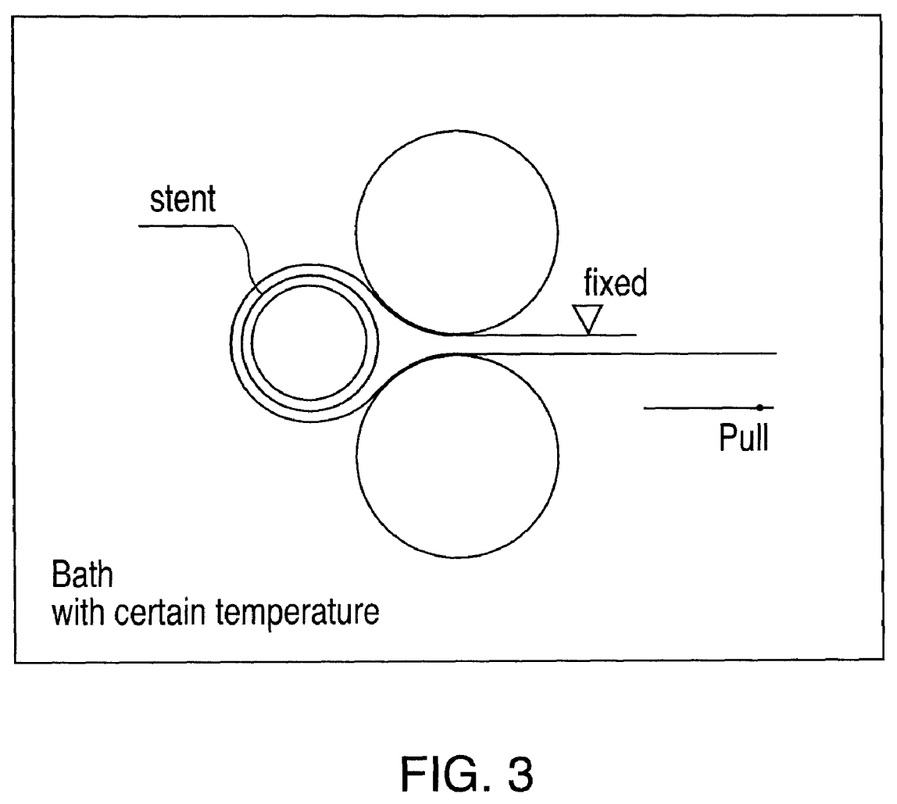
FIG. 3 is a schematic illustration showing an arrangement for inducing a TWSME in a laser-cut tubular body of a stent by collapsing the body of the stent.

FIG. 3 illustrates TWSME training of the body of a laser-cut stent by collapsing and then expanding the stent body. This procedure is preferably carried out after training of the crown segments of the stent is completed.

Once the $A_f$ temperature is between about 25° C.-35° C., the $T_R$ temperature is between about 5° C.-25° C., and the two-way recovery strain $\epsilon_{TW}$ is >0.2%, the TWSME training of the device based on an R-phase transformation can proceed.

Figure 4:
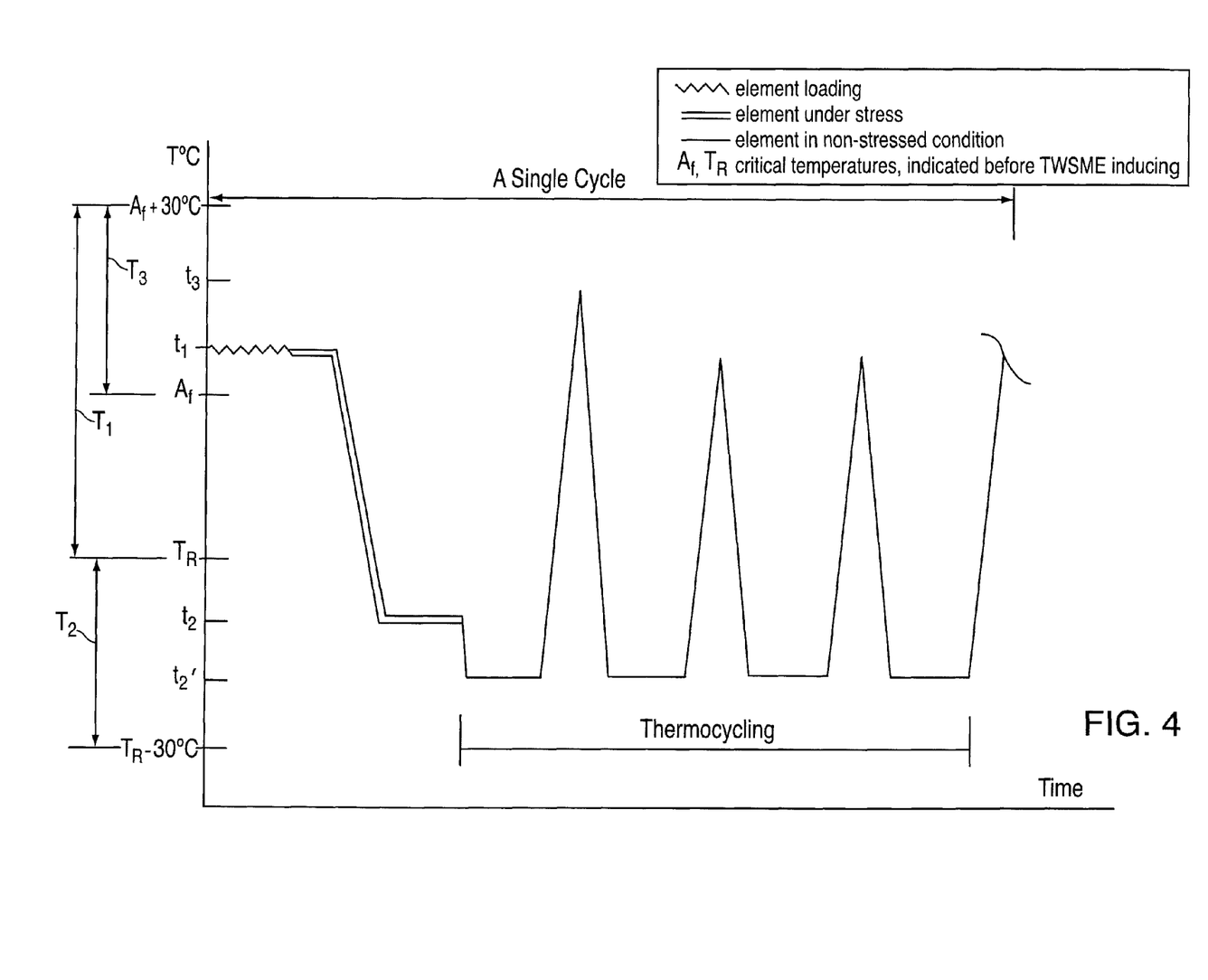
FIG. 4 is a graphical diagram illustrating a first embodiment of a method for treating a device formed of a nickel titanium alloy to obtain a TWSME based on an R-phase transformation in accordance with the invention.

Referring to FIG. 4, a first embodiment of a TWSME training process based on an R-phase transformation in accordance with the invention is illustrated. A stent crown is formed of nitinol having an $A_f$ temperature in the range of between about 25° C. and 35° C., for example 33° C., and a $T_R$ temperature in the range of between about 5° C. and 25° C., for example 6° C. The crown segment is loaded by deforming the segment of the crown of the stent on a mandrel (see FIG. 2) in its austenitic condition at a temperature $t_1$ in the range $T_1$, wherein $T_R<T_1<A_f+30°$ C., for example, 37° C. The ratio of the thickness (b) of the crown segment to the diameter (D) of the mandrel is between about 0.02 and 0.2 and the loading applies a tensile force to the crown segment of up to about 2 newtons (N). The device in its loaded condition is held at temperature $t_1$ preferably for about 1 minute and then cooled to a temperature $t_2$ in the range $T_2$, wherein $T_R-30°$ C.$<T_2<T_R$. For example, $t_2$ is $-16°$ C. The device in its loaded condition is held at a temperature $t_2$ for a certain time, preferably about 1 minute.

The device is then unloaded from the mandrel and in the illustrated embodiment, the temperature of the unloaded device is lowered to a lower temperature $t_2'$ in the range $T_2$ for example, $-23°$ C. The unloaded device is maintained at temperature $t_2'$ for a period of time, for example, 30 seconds. This temperature decrease is optional and, when used, somewhat enhances the result.

The unloaded device is then subjected to thermocycling wherein each thermocycle continues for about 1 minute and comprises heating the device to a temperature $t_3$ in the range $T_3$, wherein $A_f<T_3<A_f+30°$ C., for example, 35° C., and then cooling the unloaded device to a temperature of about $t_2'$ in the range $T_2$. The thermocycling step includes 3 to 4 thermocycles in the instant embodiment. The initial loading at a temperature in the range $T_1$, the cooling of the loaded device to a temperature in the range $T_2$, the prolonged exposure of the loaded device at temperature in the range $T_2$, and the thermocycling of the unloaded device, together constitute a single cycle (see FIG. 4). According to this embodiment, the device is subjected to a total of between about 3 to 10 cycles.

It should be noted that the $A_f$ temperature of the device in each half-cycle after exposure i.e. in the first heating step of a thermocycle after unloading increases by several degrees, by an amount determined to a large extent by stress of loading, strain i.e. b/D, and exposure time, i.e. the time under load in a constrained state.

The $A_f$ temperature drops somewhat after thermocycling in an unloaded condition. The final $A_f$ temperature may be increased up to the desirable temperature of the human body 37° C. Varying these parameters of external action can significantly affect the final temperature range over which the TWSME shape changes occur.

In accordance with the principles of the invention, in the first embodiment, internal stress fields are created inside the high-temperature phase in order to control the R-phase formation realized under cooling. The internal stress fields are generated by irreversible defects, such as dislocations caused by preliminary plastic deformation (LTMT). The oriented internal stress fields are also caused by the precipitation of the second phase particles. An additional substructure is generated as TWSME is induced due to the loading of the device and the phase transformation. After the device is unloaded, the thermocycling increases and stabilizes the two-way recovery strain $\epsilon_{TW}$ as well as the temperature range over which the TWSME is manifested.

A TWSME can then be induced in the body of the stent in the manner shown in FIG. 3 by collapsing and expanding the stent using the special equipment in accordance with the time—temperature regime for inducing a TWSME as shown in FIG. 4.

Figure 5:
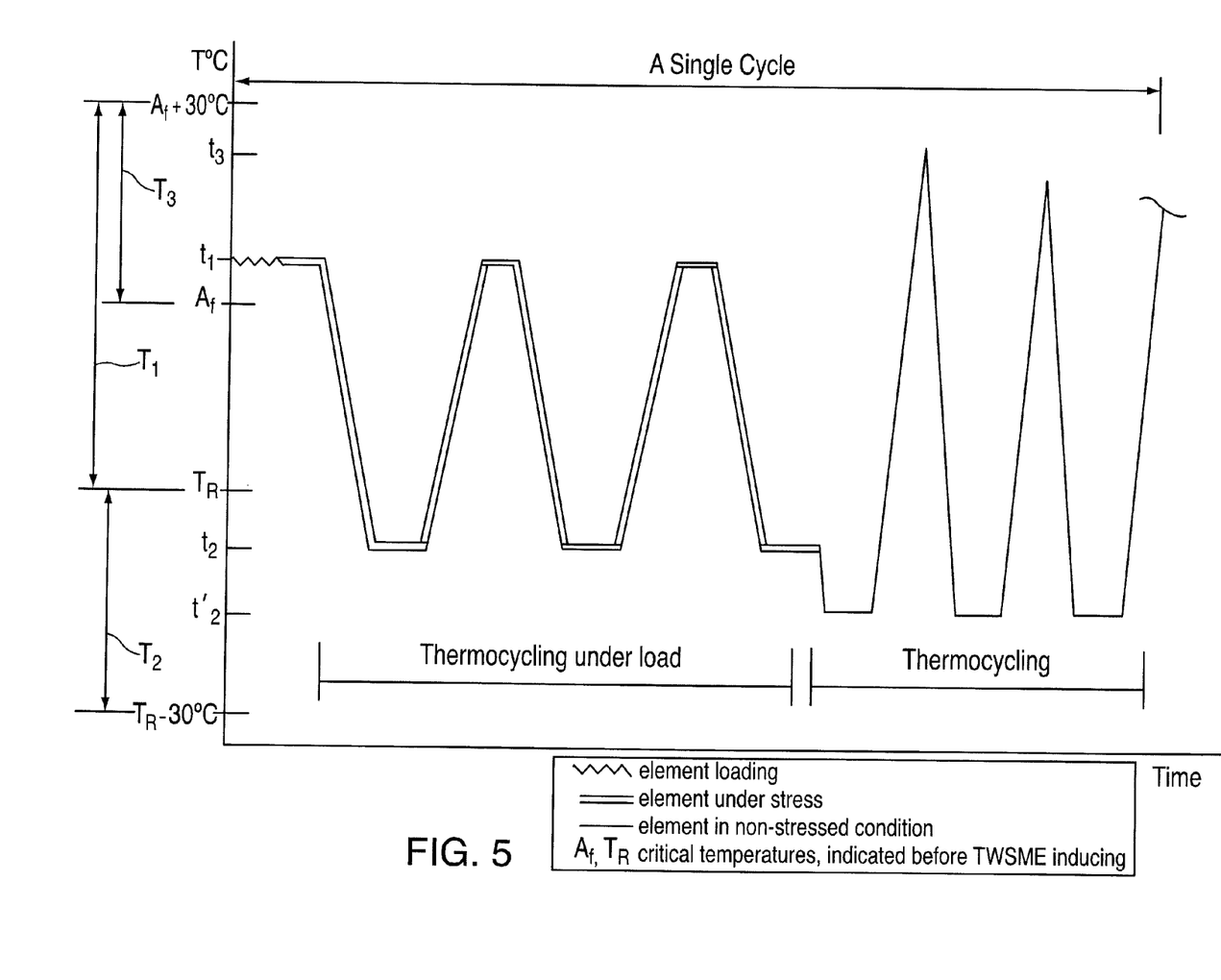
FIG. 5 is a graphical diagram illustrating a second embodiment of a method for treating a device formed of a nickel titanium alloy to obtain a TWSME based on an R-phase transformation in accordance with the invention.

A second embodiment of a process for inducing a TWSME in a segment of a crown of a stent is shown in FIG. 5. In accordance with the invention, the stent crown is formed of nitinol having an $A_f$ temperature in the range of between about 25° C. to 35° C., for example 30° C., and a $T_R$ temperature in the range of between about 5° C. to 25° C., for example 6° C. The crown segment is loaded on a mandrel (see FIG. 2) at a temperature $t_1$ in the range $T_1$, wherein $T_R<T_1<A_f+30°$ C., for example 32° C. The loading applies a tensile force of up to 2N. The loaded element is then cooled to a temperature $t_2$ in the range $T_2$, wherein $T_R-30°$ C.$<T_2<T_R$, for example $-15°$ C., and maintained at this temperature for about 1 minute. The element in its loaded condition is then subjected to thermocycling wherein each thermocycle comprises heating the loaded element to a temperature in the range $T_1$, for example 32° C., and then cooling the loaded element to a temperature in the range $T_2$, for example, $-15°$ C. The thermocycling under load includes between two and ten thermocycles.

The crown segment is then unloaded and subjected to thermocycling. Prior to thermocycling, the temperature of the unloaded segment is reduced to a temperature $t_2'$ in the range $T_2$, for example, 24° C., although this reduction in temperature is optional. Each thermocycle comprises heating the unloaded segment to a temperature $t_3$ in the range $T_3$, wherein $A_f<T_3<A_f+30°$ C., for example, 37° C., and then cooling the unloaded segment to a temperature $t_2'$ in the range $T_2$, wherein $T_R-30°$ C.$<T_2<T_R$, for example $-24°$ C. The thermocycling includes at least 3 thermocycles.

The thermocycling under load followed by unloading and thermocycling together constitute a single cycle. According to the invention, the element is subject to between about 3 to 10 cycles, for example 8 cycles.

This embodiment of the invention is based on thermocycling through a temperature range in which a B2$\leftrightarrow$R-phase transformation occurs under constant stress. The method induces a TWSME in the device due to the appearance, development and stabilization upon thermocycling of the phase transformation induced dislocation substructure ("transformation-induced hardening") which is in addition to the dislocation substructure created in the LTMT and subsequent ageing process. Again, variations in external parameters, such as stress, strain and exposure time, can significantly affect the properties of the TWSME.

Figure 6:
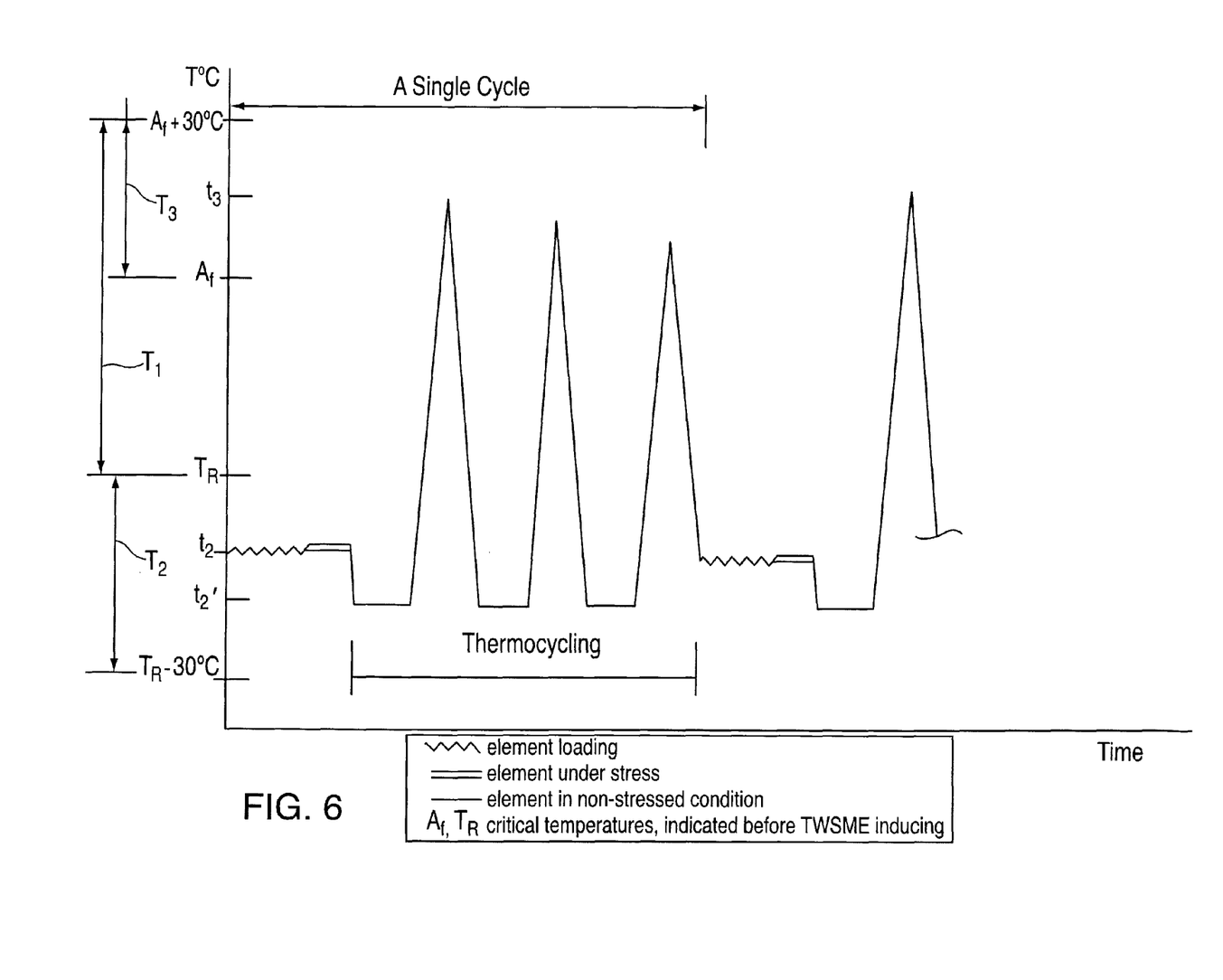
FIG. 6 is a graphical diagram illustrating a third embodiment of a method for treating a device formed of a nickel titanium alloy to obtain a TWSME based on an R-phase transformation in accordance with the invention.

A third embodiment of a process for including a TWSME in a SMA is illustrated in FIG. 6. The device is formed of nitinol having an $A_f$ temperature in the range of between about 25° C. to 35° C., for example 28° C., and a $T_R$ temperature in the range of between about 5° C. to 25° C., for example 10° C.

In this embodiment, the device is initially deformed on a mandrel beyond a certain limiting strain in the R-phase at a temperature $t_2$ in the range $T_2$, wherein $T_R-30°$ C.$<T_2<T_R$, for example $-15°$ C. The loading applies a tensile force of up to 2N. The loaded device is maintained at a temperature $t_2$ in the range $T_2$ for about 1 minute whereupon the device is unloaded and cooled to a temperature $t_2'$ in the range $T_2$, a few degrees below the initial $T_2$ temperature $t_2$. The unloaded device is then subjected to thermocycling in which each thermocycle includes heating the unloaded device to a temperature $t_3$ in the range $T_3$, wherein $A_f<T_3<A_f+30°$ C., for example 37° C., and cooling the unloaded device to a temperature in the range $T_2$, such as $t_2'$. The thermocycling includes between about 3 to 10 thermocycles, for example 3 thermocycles. The initial loading and unloading of the device followed by thermocycling of the unloaded device constitutes a single cycle. According to the invention, the element is subjected to between about 3 to 10 cycles, for example 7 cycles. Again, variations in external parameters such as stress, strain and exposure times can significantly affect the properties of the TWSME.

As noted above, the parameters of TWSME induced using conventional training generally are not thermally stable. In particular, the two-way effect degrades when a device is heated above the $A_f$ temperature and does not recover completely with repeated testing in the initial temperature range.

In accordance with the present invention, in order to provide thermal and long-term stabilization of TWSME parameters in a nickel-titanium based alloy device based on an R-phase transformation, the device is fixed on a special mandrel in its second shape (the shape corresponding to the R-phase transformation) and is then cooled to a temperature which is less than $T_R$ and exposed at that temperature for about 1-30 days. Alternatively, the device can be cooled without a mandrel to said temperature and exposed to said temperature. After the exposure is completed, the TWSME parameters become thermally stable up to about 100° C. and acquire a practically unlimited long-term stability. In that case, some lattice accommodation and additional TWSME training takes place.

EXAMPLE 1

The method of the first embodiment of the invention is utilized to induce a TWSME in the segments of a crown of an endovascular stent. The device is constituted by a super-elastic tube having an external diameter of 8 mm and an internal diameter of 7.52 mm, and is made from a Ni—Ti alloy wherein the atomic weight percentage of Ni is 50.7% and the atomic weight percentage of Ti is 49.3%. The $A_s$ and $A_f$ temperatures of the device were determined thermomechanically and the $A_s$ temperature was 13° C. and the $A_f$ temperature was 27° C.

The stent was fixed on a cylindric mandrel and then heated in a furnace to a temperature of 430° C. in a vertical position for 1.5 hours. Thereafter, the tube was subjected to quenching in water to room temperature.

The $A_f$ temperature was measured thermomechanically and the $A_f$ temperature was 34° C. Next, the possibility of TWSME training was tested. One crown segment (of six) was bent around a mandrel shown in FIG. 2(a) with the tube immersed in a bath at 5° C. for 10 seconds. The crown segment was then unloaded and the tube immersed in a bath at a temperature of 35° C. with a control of full shape recovery. Then the tested device is again placed in a bath at a temperature of about 5° C. without being loaded on a mandrel. The diameter of the arch generated by the device was measured and the ratio of the device thickness to the arch radius was calculated to be 0.5%.

A procedure of inducing TWSME in the device in accordance with the first embodiment of the invention shown in FIG. 4 was then initiated. One of the six crown segments bent around a mandrel having a diameter of about 2.5 mm as seen in FIG. 2(a) is placed in a bath at a temperature of 36° C. and exposed for about 10 seconds. While still loaded on the mandrel, the device was immersed in a bath at a temperature of 0° C. and exposed for 30 seconds whereupon the device was unloaded from the mandrel and placed in a bath at −10° C. for 10 seconds. The unloaded device was then placed in a bath at 36° C. with a control of full shape recovery. The shape recovery was seen not to be complete and the bath temperature was increased to 37° C., at which temperature the device manifested full shape recovery. The device was then placed in a bath at −10° C. for 10 seconds and then in a bath at 35 C° for 5 seconds with a control of full shape recovery. This thermocycling was repeated three times. The temperature of full shape recovery was checked in every cycle of the thermocycling and it was noted that it dropped to 35° C. in the second cycle and remained the same in the third cycle.

As noted in FIG. 4, the foregoing steps constitute a single cycle of TWSME inducing. After 3 such cycles, the two-way recovery strain was 1.3%.

The above-procedure was repeated for each of the six segments of the stent crown. The procedure was deemed completed when the ends of all of the crown segments moved into proximity with each other (a "closed" condition) in the clearance of the stent.

The stent with the "closed" crown was put into a container, then placed into a freezing room at a temperature of −18° C. and exposed for three days.

A TWSME was then induced in the body of the stent. The procedure was performed in the manner shown in FIG. 3 by collapsing and expanding the stent using special equipment in accordance with the time-temperature regimens for inducing a TWSME depicted in FIG. 4.

The TWSME induced in the crown segments and body of the stent was checked. The stent with the crown in its "closed" condition and at a minimum body diameter was placed in a container which was placed in a cold store at a temperature of −18° C. where it was exposed for three days.

EXAMPLE 2

The method of the second embodiment of the invention is utilized to induce a TWSME in the crown of an endovascular stent. The device is constituted by a super-elastic tube having an external diameter of 10 mm and an internal diameter of 9.2 mm, and is made from a Ni—Ti alloy wherein the atomic weight percentage of Ni is 50.7% and the atomic weight percentage of Ti is 49.3%. The $A_s$ and $A_f$ temperatures of the device were determined thermomechanically and the $A_s$ temperature was 15° C. and the $A_f$ temperature was 29° C.

The stent was fixed on a cylindric mandrel and then heated in a furnace to a temperature of 440° C. in a vertical position for 2 hours. Thereafter, the tube was subjected to quenching in water to room temperature.

The $A_f$ temperature was measured thermomechanically and the $A_f$ temperature was 32° C. Next, the possibility of TWSME training was tested. One crown segment (of six) was bent around a mandrel shown in FIG. 2(a) with the tube immersed in a bath at 0° C. for 30 seconds. The crown segment was then unloaded and the tube with the stent on it immersed in a bath at a temperature of 33° C. with a control of full shape recovery. Then the tested device is again placed in a bath at a temperature of about 5° C. without being loaded on a mandrel. The diameter of the arch generated by the device was measured and the ratio of the device thickness to the arch radius was calculated to be 0.6%.

A procedure of inducing TWSME in the device in accordance with the second embodiment of the invention shown in FIG. 5 was then initiated. All six crown segments bent around a mandrel having the diameter of 2.0 mm as seen in FIG. 2(a) were placed in a bath at a temperature of 36° C. ($t_1$) and exposed for about 10 seconds. While still loaded on the mandrel, the device was immersed in a bath at a temperature of 0° C. ($t_2$), exposed for 30 seconds and then subjected to thermocycling. The device was then unloaded from the mandrel and placed in a bath at −10° C. ($t_{2'}$) for 10 seconds. The unloaded device was then placed in a bath at 36° C. with a control of full shape recovery. The shape recovery was seen not to be complete and the bath temperature was increased to 37° C. ($t_3$), at which temperature the device manifested full shape recovery. The device was then placed in a bath at −10° C. ($t_{2'}$) for 10 seconds and then in a bath at 35° for 5 seconds with a control of full shape recovery. This thermocycling was repeated three times. The temperature of full shape recovery was checked in every cycle of the thermocycling and it was noted that it dropped to 35° C. in the second cycle and remained the same in the third cycle.

As noted in FIG. 5, the foregoing steps constitute a single cycle of TWSME inducing. After 7 such cycles, the two-way recovery strain was 1.5% and the procedure was completed.

The procedure was deemed completed when the ends of all of the crown segments moved into proximity with each other (a "closed" condition) in the clearance of the stent.

The stent with the "closed" crown was put into a container, then placed into a freezing room at a temperature of −18° C. and exposed for 24 hours.

A TWSME was then induced in the body of the stent. The procedure was performed in the manner shown in FIG. 3 by collapsing and expanding the stent using special equipment in accordance with the time-temperature regimens for inducing a TWSME depicted in FIG. 5.

The TWSME induced in the crown segments and body of the stent was checked. The stent with the crown in its "closed" condition and at a minimum body diameter was placed in a container which was placed in a cold store at a temperature of −18° C. where it was exposed for 24 hours.

EXAMPLE 3

The method of the third embodiment of the invention is utilized to induce a TWSME in the segments of a crown of an endovascular stent. The device is constituted by a superelastic tube having an external diameter of 8 mm and an internal diameter of 7.52 mm, and is made from a Ni—Ti alloy wherein the atomic weight percentage of Ni is 50.7% and the atomic weight percentage of Ti is 49.3%. The $A_s$ and $A_f$ temperatures of the device were determined thermomechanically and the $A_s$ temperature was 13° C. and the $A_f$ temperature was 27° C.

The stent was fixed on a cylindric mandrel and then heated in a furnace to a temperature of 400° C. in a vertical position for 10 hours. Thereafter, the tube was subjected to quenching in water to room temperature.

The $A_f$ temperature was measured thermomechanically and the $A_f$ temperature was 34° C. Next, the possibility of TWSME training was tested. One crown segment (of six) was bent around a mandrel shown in FIG. 2(b) with the tube immersed in a bath at 5° C. for 30 seconds. The crown segment was then unloaded and the tube immersed in a bath at a temperature of 35° C. with a control of fall shape recovery. Then the tested device is again placed in a bath at a temperature of about 5° C. without being loaded on a mandrel. The diameter of the arch generated by the device was measured and the ratio of the device thickness to the arch radius was calculated to be 0.5%.

A procedure of inducing TWSME in the device in accordance with the third embodiment of the invention shown in FIG. 6 was then initiated. One of the six crown segments bent around a mandrel having the diameter of 2.0 mm under tensile force of 2 newtons as seen in FIG. 2(b) is placed in a bath at a temperature of 0° C. ($t_2$) and exposed for about 60 seconds under tensile. The device was then unloaded and immersed in a bath at a temperature of −20° C. ($t_{2'}$) and exposed for 10 seconds. The device was then placed in a bath at 34° C. with a control of full shape recovery. The shape recovery was seen not to be complete and the bath temperature was increased to 36° C. ($t_{2'}$), at which temperature the device manifested full shape recovery. The device was then placed in a bath at −20° C. for 10 seconds and then in a bath at 35° for 5 seconds with a control of full shape recovery. This thermocycling was repeated three times. The temperature of full shape recovery was checked in every cycle of the thermocycling and it was noted that it dropped to 35° C. in the second cycle and remained the same in the third cycle.

As noted in FIG. 6, the foregoing steps constitute a single cycle of TWSME inducing. After 3 such cycles, the two-way recovery strain was 1.6%.

The above-procedure was repeated for each of the six segments of the stent crown. The procedure was deemed completed when the ends of all of the crown segments moved into proximity with each other (a "closed" condition) in the clearance of the stent.

The stent with the "closed" crown was put into a container, then placed into a freezing room at a temperature of −18° C. and exposed for two days.

A TWSME was then induced in the body of the stent. The procedure was performed in the manner shown in FIG. 6 by collapsing and expanding the stent using special equipment in accordance with the time-temperature regimens for inducing a TWSME depicted in FIG. 6.

The TWSME induced in the crown segments and body of the stent was checked. The stent with the crown in its "closed" condition and at a minimum body diameter was placed in a container which was placed in a cold store at a temperature of −18° C. where it was exposed for 24 hours.

Obviously, numerous modifications and variations of the present invention are possible in light of the specification. It is therefore to be understood that within the scope of the claims, the invention may be practiced otherwise than as specifically disclosed herein.

What is claimed is:

1. A process for treating a device formed of nickel-titanium based alloy having an $A_f$ temperature in the range of between about 25° C.-35° C., and a $T_R$ temperature in the range of between about 5° C.-25° C., said device exhibiting a one-way shape memory effect in which it spontaneously transforms from an initial shape in the austenitic phase to a final shape in the R-phase, so that the device exhibits a two-way shape memory effect (TWSME) based on a reversible R-phase transformation, comprising the steps of:
    (a) loading said device at a temperature in a range $T_1$, wherein $T_R<T_1<A_f+30°$ C.;
    (b) cooling said device in its loaded condition to a temperature in a range $T_2$, wherein $T_R-30°$ C.$<T_2<T_R$;
    (c) unloading said device at a temperature in the range $T_2$;
    (d) thermocycling said unloaded device several times, wherein each thermocycle includes, (1) heating said unloaded device to a temperature in a range $T_3$, wherein $A_f<T_3<A_f+30°$ C.; and (2) cooling said unloaded device to a temperature in the range $T_2$.

2. A process according to claim 1 wherein said step of thermocycling comprises subjecting said unloaded device to between about 3 to 10 thermocycles.

3. A process according to claim 1 wherein step (a) further comprises maintaining said device in a loaded condition at a temperature in the range $T_1$ for about 1 minute.

4. A process according to claim 1 wherein step (b) further comprises maintaining said device in a loaded condition at a temperature in the range $T_2$ for about 1 minute.

5. A process according to claim 1 wherein said loading in step (a) comprises bending the device around a mandrel.

6. A process according to claim 5 wherein the device is an elongate member and the ratio of the thickness or diameter of said device to the diameter of said mandrel is between about 0.02 and 0.2.

7. A process according to claim 1 wherein said loading in step (a) applies a tensile force to said device of up to about 2 newtons.

8. A process according to claim 1 wherein each thermocycle continues for about 1 minute.

9. A process according to claim 1 wherein said device comprises a laser cut stent.

10. A process according to claim 9 wherein said loading in step (a) comprises collapsing the body of the stent.

11. A process according to claim 1 wherein said device comprises a segment of a crown of a stent.

12. A process according to claim 1 further comprising repeating steps (a)-(d) about 3 to 10 times.

13. A process for treating a device formed of a nickel-titanium based alloy having an $A_f$ temperature in the range of between about 25° C.-35° C. and a $T_R$ temperature in the range of between about 5° C.-25° C., said device exhibiting a one-way shape memory effect in which it spontaneously transforms from an initial shape in the austenitic phase to a final shape in the R-phase, so that the device exhibits a two-way shape memory effect (TWSME) based on a reversible R-phase transformation, comprising the steps of:

loading said device at a temperature in a range $T_1$, wherein $T_R<T_1<A_f+30°$ C.;

(a) cooling said device in its loaded condition to a temperature in a range $T_2$, wherein $T_R-30°$ C.$<T_2<T_R$;

(b) thermocycling said device several times in its loaded condition, wherein each thermocycle includes (1) heating said device in its loaded condition to a temperature in a range $T_3$, wherein $A_f<T_3<A_f+30°$ C.; and (2) cooling said device in its loaded condition to a temperature in the range $T_2$;

(c) unloading said device at a temperature in the range $T_2$;

(d) thermocycling said device several times in its unloaded condition, wherein each thermocycle includes (1) heating said device in its unloaded condition to a temperature in the range $T_3$, and (2) cooling said device in its unloaded condition to a temperature in the range $T_2$.

14. A process according to claim 13 wherein said step (c) of thermocycling comprises subjecting said device in its loaded condition to between about 3 to 10 thermocycles.

15. A process according to claim 13 wherein said step (e) of thermocycling comprises subjecting said device in its unloaded condition to between about 3 to 10 thermocycles.

16. A process according to claim 13 wherein step (a) further comprises maintaining said loaded device at a temperature in the range $T_1$ for about 1 minute.

17. A process according to claim 13 wherein step (b) further comprises maintaining said loaded device at a temperature in the range $T_2$ for about 1 minute.

18. A process according to claim 13 wherein said loading in step (a) comprises bending the device around a mandrel.

19. A process according to claim 18 wherein the device is an elongate member and the ratio of the thickness or radius of said device to the diameter of said mandrel is between about 0.02 and 0.2.

20. A process according to claim 13 wherein said loading in step (a) applies a tensile force to said device of up to about 2 newtons.

21. A process according to claim 13 wherein each exposure of the device in its loaded condition at temperatures in the ranges of $T_1$ and $T_2$ continues for about 1 minute.

22. A process according to claim 13 wherein said device comprises a laser cut stent.

23. A process according to claim 22 wherein said loading in step (a) comprises collapsing the body of the stent.

24. A process according to claim 13 wherein said device comprises a segment of a crown of a stent.

25. A process according to claim 13 further comprising repeating said steps (a)-(e) about 2 to 10 times.

26. A process for treating a device formed of a nickel-titanium based alloy having an $A_f$ temperature in the range of between about 25° C.-35° C. and a $T_R$ temperature in the range of between about 5° C.-25° C., said device exhibiting a one-way shape memory effect in which it spontaneously transforms from an initial shape in the austenitic phase to a final shape in the R-phase, so that the device exhibits a two-way shape memory effect (TWSME) based on a reversible R-phase transformation, comprising the steps of:

loading said device at a temperature in a range $T_2$, wherein $T_R-30°$ C.$<T_2<T_R$;

unloading said device at a temperature in the range $T_2$;

(a) thermocycling said unloaded device several times, wherein each thermocycle includes, (1) heating said device in its unloaded condition to a temperature in a range $T_3$, wherein $A_f<T_3<A_f+30°$ C.; and (2) cooling said device in its unloaded condition to a temperature in the range $T_2$.

27. A process according to claim 26 wherein said step of thermocycling comprises subjecting said unloaded device to between about 3 to 10 thermocycles.

28. A process according to claim 26 wherein said step (a) further comprises maintaining said device in a loaded condition at a temperature $T_2$ for about 1 minute.

29. A process according to claim 26 wherein said loading in step (a) comprises bending the device around a mandrel.

30. A process according to claim 29 wherein the device is an elongate member and the ratio of the thickness or radius of said device to the diameter of said mandrel is between about 0.02 and 0.2.

31. A process according to claim 26 wherein said loading in step (a) applies a tensile force to said device of up to about 2 newtons.

32. A process according to claim 26 wherein said device comprises a laser cut stent.

33. A process according to claim 32 wherein said loading in step (a) comprises collapsing the body of the stent.

34. A process to claim 26 wherein said device comprises a segment of a crown of a stent.

35. A process according to claim 26 further comprising repeating said steps (a)-(c) about 2 to 10 times.

* * * * *